United States Patent [19]

Kunst et al.

[11] Patent Number: 5,246,722
[45] Date of Patent: Sep. 21, 1993

[54] PREPARATION OF CONCENTRATES OF COLORING AGENTS

[75] Inventors: Anthonie Kunst, Huizen; Marcellinus J. J. Hakkaart, Hilversum, both of Netherlands

[73] Assignee: Unilever Patent Holdings B.V., London, England

[21] Appl. No.: 693,298

[22] Filed: May 1, 1991

[30] Foreign Application Priority Data

May 1, 1990 [EP] European Pat. Off. ........ 90304727.2
Mar. 19, 1991 [GB] United Kingdom ................ 9105764

[51] Int. Cl.$^5$ .............................................. A23L 1/277
[52] U.S. Cl. .................................... 426/540; 426/250; 426/429; 585/864; 585/800; 203/38; 203/28; 8/506; 8/646; 8/637.1
[58] Field of Search ............. 426/250, 540, 429; 585/864, 800; 203/38, 28; 8/506, 646, 637.1

[56] References Cited

U.S. PATENT DOCUMENTS 5,019,668  5/1991  Keat et al. ............................ 585/864
5,039,536  8/1991  Vunsh et al. ......................... 426/540

FOREIGN PATENT DOCUMENTS 0242148  12/1990  European Pat. Off. .
74349    4/1954   Netherlands .

OTHER PUBLICATIONS

Japanese Abstracts for Applns. J 51144714A and J51144715A.
Landen et al., J. Assoc. Off. Anal. Chem., 62:2, 283–289 (1979).
Fraser et al., JAOCS, 58:10, 926–931 (1981).
Ong et al., Palm Oil Prod. Technol. Eighties, Rep. Proc. Int. Conf. 1981.

Primary Examiner—Jeanette Hunter
Attorney, Agent, or Firm—Cushman, Darby & Cushman

[57] ABSTRACT

Concentrates of natural coloring agents such as carotene are prepared from organic media, particularly from palm oil, by a process in which the oil, together with a volatile solvent, is subjected to gel permeation chromatography. The concentrated coloring agent may then be used in food products such as margarine and ice cream.

4 Claims, No Drawings

PREPARATION OF CONCENTRATES OF COLORING AGENTS

This invention relates to the preparation of concentrates of natural colouring agents from naturally derived organic media and in particular the separation of carotene from natural oils, oils derived from genetically engineered plant material, and from organic media comprising fatty acids and fatty acid esters which may have been derived from such oils.

Carotenes are widely used as colouring agents in foods and can be obtained by recovery from natural oils or by synthesis. Although they represent a high commercial value, the carotenes are destroyed during the oil refining process which is necessary to remove components like gums, free fatty acids and off-flavours which are undesired in the further oil processing and in the food application of natural oils and fats.

Preparation of concentrates of the colouring agents from the oil without degrading the oil has not to date been achieved in a commercially successful manner. Attempted methods to recover carotenoids from oil depend on either chemical modification of the oil, the use of adsorbent materials, progressive fractionation with solvents of the oil, or on molecular distillation.

European patent specification EP 242148A (Lion Corporation) describes a method of purifying a carotene-containing concentrate from a source such as palm oil by adsorption chromatography in which the palm oil is firstly subjected to alcoholysis and is then passed to an adsorption chromatography column containing a silica gel or activated alumina filler. This process suffers from the disadvantage that the triglycerides in the oil are chemically transformed and cannot be used any more in food applications like e.g. fat spreads.

Several methods using adsorbent materials like activated carbon have been described (Dutch patent 74349, Ong et al in Palm Oil Prod. Technol. Eighties, Rep. Proc. Int. Conf. 1981).

These methods suffer from the disadvantage that elution of the carotenes from the adsorbent can only be achieved effectively with aromatic solvents which are not suitable for the production of food ingredients.

Japanese patent applications J 51144714A and J 51144715A (Riken Vitamin Oil KK) describe methods for the purification of tocopherol, another minor ingredient of some vegetable oils, by gel permeation chromatography using hydrocarbon or alcohol solvents. In the described processes the scum of the oil deoderisation process is used as raw material. Unfortunately the carotenoids in the oil are destroyed or modified during the deoderisation; the described process therefore is not suited for the recovery of carotenes.

Landen & Eitenmiller in J. Assoc. Off. Anal. Chem. (Vol. 62 No. 2, 1979) describe the application of high pressure gel permeation chromatography for the analyses of the beta-carotene and the retinyl palmitate content in oil. The method is based on the simultaneous measurement of the refractive index and the absorbance at 340 nm and 436 nm of the effluent of the chromatography column. No separation of the oil and the carotenoid fraction is achieved however, which makes this process unsuited for the recovery of carotenoids from oil.

It is an object of this invention to prepare concentrates of natural colouring agents from naturally derived organic media in such a manner that the colouring agent can subsequently be used as a food ingredient and in such a manner that the organic medium is not degraded.

We have now surprisingly found that gel permeation chromatography can be used in a commercially successful manner to extract carotene from palm oil without first chemically modifying the oil and from other natural oils as well as from media comprising fatty acids and/or fatty acid esters derived from such oils.

Thus, according to the invention there is provided a process for the preparation of concentrates of natural colouring agents from organic media selected from fatty acid glycerides derived from natural sources, including genetically engineered plant material, media comprising fatty acids and fatty acid esters in which the organic medium, together with a volatile solvent, is subjected to gel permeation chromatography.

To run the process in a commercially successful manner the process is preferably carried out at an elevated temperature. We have found that a suitable temperature is from 30 to 80° C. such as from 55° C. to 65° C., most preferably about 60° C.

The choice of volatile solvent is linked to the nature of the column material.

For separations with gel permeation the molecular weights of the components to be separated should ideally be within the useful molecular weight working range of the gel bed. In general a gel bed has to be chosen such that the components with the highest molecular weight elute at or near the void volume.

Suitable column materials include cross-linked polystyrene polymers, cross-linked dextrans cross-linked agaroses, cross-linked celluloses, silica gel and modified silica gels.

The solvent should be volatile, to enable its removal by distillation without degrading the colouring agent being concentrated. Suitable solvents include hexane, cyclohexane, butylacetate, iso-propyl alcohol, methyl ethyl ketone, acetone, ethanol, water and mixtures thereof. Further, the solvent should be such that any traces thereof remaining in the colouring agent concentrate are acceptable in food products.

While the process according to the invention is particularly applicable to the extraction of carotene from palm oil, other colouring agents can be extracted from other natural oils using the same process. Further embodiments of the invention include the extraction of capsanthin and capsorubin from paprika oleoresin.

The process according to the invention is also applicable to the concentration of colouring agents from organic media comprising fatty acids such as palmitic and stearic acids and mixtures thereof which are obtained from a natural oil, such as by conventional fat splitting techniques. Organic media comprising esters of such fatty acids, in particular methyl and ethyl esters may also be subjected to the process.

In practice the column material is fully swollen with the same solvent as will be used for elution. After swelling the column is packed. The organic medium or a mixture thereof with solvent is then added to the top of the column.

We have found that if, when using polystyrene or dextran polymers as column material, no solvent is included in the organic liquid at this stage the column material tends to shrink, causing unpredictable results. A suitable organic medium to solvent ratio is up to 5:1, such as from 2:1 to 1:2, preferably about 1:1 by weight.

As a result of the differential permeation rate of the various molecules in the sample, separation occurs in the column upon elution with the solvent resulting in a number of fractions. Starting with a natural oil or starting with a medium comprising fatty acids and/or fatty acid esters containing, for example, up to 1000 ppm colouring agent, a fraction with a concentration of at least 0.5% up to 25% by weight can be produced by this method. The solvent is removed from this, and other fractions eluted from the column, by distillation and may usefully be recycled.

The invention enables the production of a natural carotene concentrate comprising at least 0.5% by weight carotene.

The concentrated colouring agent may be used as such as a food additive or it may be further processed as desired. The concentrate will often be enriched in mono-and diglycerides and in tocopherols. These materials may give the product added value according to its intended end use. This invention also enables the provision of a manufactured food product containing the natural carotene concentrate obtained in this way.

The organic medium from which the colouring agent has been removed may be further processed as desired.

The invention will now be illustrated by the following example.

EXAMPLE

A gel permeation chromatography column having a diameter of 25 mm. and fitted with a heating jacket was used. The column was packed with 75 g resin which had been preswollen in ethyl actetate giving a column height of 50cm. The resin was a polystyrene polymer with divinylbenzene crosslinkages, commercially available as Bio-Beads S-X3 from Bio-Rad Laboratories. The column was heated to 60° C. and 12g sample of a 1:1 mixture of ethyl acetate and crude palm oil was loaded on top of the column. The column was eluted with ethyl acetate at a linear flow rate of 0.65 cm/min.

The crude palm oil was mainly in the form of tri-, di- and monoglycerides but also contains a number of minor ingredients including from 500 to 1000 ppm carotene. The eluted fraction contained 90% of the total carotenes. The ethyl acetate was removed from this fraction by distillation to yield a solution of at least 0.5% carotene in an oil base which is suitable for use as a food colouring additive for various manufactured food products such as margarine and ice cream.

EXAMPLE 2

A gel permeation chromatography column, having a diameter of 25 mm and fitted with a heating jacket was used. The column was packed with 85 gram resin which had been preswollen in methyl ethyl ketone giving a column height of 50 cm. The resin was a polystyrene polymer with divinylbenzene crosslinkages, commercially available as Bio-Beads S-X4 from Bio-Rad Laboratories.

The column was heated to 60° C. and a 12 gram sample of a 1:1 mixture of methyl ethyl ketone and crude palm oil was loaded on top of the column. The column was eluted with methyl ethyl ketone at a linear flow rate of 0.65 cm/min.

The crude palm oil was mainly in the form of tri-, di- and monoglycerides but also contains a number of minor ingredients including from 500 to 1000 ppm carotene. The eluted fraction contained 90% of the total carotenes. The methyl ethyl ketone was removed from this fraction by distillation to yield a solution of at least 0.5% carotene in an oil base which is suitable for use as a food colouring additive for various food products such as margarine and ice cream.

EXAMPLE 3

A gel permeation chromatography column, having a diameter of 25 mm and fitted with a heating jacket was used. The column was packed with 75 gram Bio-Beads SX-3 which had been preswollen in ethyl acetate giving a column height of 50 cm.

The column was heated to 40° C. and a 10 gram sample of a mixture comprising ethyl acetate (50%), linoleic acid (12.5%), oleic acid (37.5%) and carotene (800 ppm) was loaded on top of the column. The column was eluted with ethyl acetate at a linear flow rate of 0.58 cm/min.

A fraction containing 90% of the total carotenes can be collected. The ethyl acetate was removed from this fraction by distillation to yield a solution of at least 0.5% carotene which is suitable for use as a food colouring additive for various food products such as margarine and ice cream.

We claim:

1. A process for the preparation of a concentrate of a natural colouring agent from an organic medium selected from fatty acid glycerides derived from natural sources, and media containing fatty acids and fatty acid esters derived therefrom, in which said organic medium, together with a volatile solvent selected from hexane, cyclohexane, butylacetate, ethyl acetate, isopropyl alcohol, methyl ethyl ketone, acetone, ethanol, water and mixtures thereof, is subjected to gel permeation chromatography at a temperature of from 30° C. to 80° C.

2. A process according to claim I, carried out at an temperature of from 55° C. to 65° C.

3. A process according to claim 1, in which the natural colouring agent is carotene.

4. A process according to claim 1, in which the organic medium is palm oil.

* * * * *